(12) United States Patent
Pielhop et al.

(10) Patent No.: US 9,611,494 B2
(45) Date of Patent: Apr. 4, 2017

(54) USE OF CARBONIUM ION SCAVENGERS IN THE TREATMENT OF LIGNOCELLULOSIC BIOMASS

(71) Applicant: ETH Zurich, Zurich (CH)

(72) Inventors: Thomas Pielhop, Zurich (CH);
Michael Hans-Peter Studer, Aetingen (CH); Philipp Rudolf von Rohr, Muttenz (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 14/356,625

(22) PCT Filed: Nov. 5, 2012

(86) PCT No.: PCT/EP2012/004599
§ 371 (c)(1),
(2) Date: May 7, 2014

(87) PCT Pub. No.: WO2013/068092
PCT Pub. Date: May 16, 2013

(65) Prior Publication Data
US 2014/0312270 A1    Oct. 23, 2014

(30) Foreign Application Priority Data

Nov. 8, 2011 (EP) .................................. 11008860

(51) Int. Cl.
| | |
|---|---|
| D21B 1/02 | (2006.01) |
| C12P 19/02 | (2006.01) |
| D21C 3/22 | (2006.01) |
| D21C 1/02 | (2006.01) |
| D21C 5/00 | (2006.01) |
| C12P 19/14 | (2006.01) |

(52) U.S. Cl.
CPC .............. *C12P 19/02* (2013.01); *C12P 19/14* (2013.01); *D21C 1/02* (2013.01); *D21C 3/222* (2013.01); *D21C 5/005* (2013.01); *C12P 2201/00* (2013.01)

(58) Field of Classification Search
CPC . D21B 1/021; D21B 1/12; D21B 1/16; D21C 1/02
USPC ....................... 162/21, 22, 65, 70, 76, 77, 82
See application file for complete search history.

(56) References Cited

U.S. PATENT DOCUMENTS

| | | | |
|---|---|---|---|
| 6,770,168 B1 | 8/2004 | Stigsson | |
| 7,906,687 B2 | 3/2011 | Voitl et al. | |
| 2010/0121110 A1* | 5/2010 | Voitl et al. | 568/426 |
| 2013/0045509 A1* | 2/2013 | Romero | 435/99 |

FOREIGN PATENT DOCUMENTS

| | | | | |
|---|---|---|---|---|
| ES | 1130085 A1 * | 9/2001 | ................ | C12P 7/10 |
| WO | 0047812 A1 | 8/2000 | | |
| WO | 2008106811 A1 | 9/2008 | | |

OTHER PUBLICATIONS

Alvira, P. et al., Pretreatment technologies for an efficient bioethanol production process based on enzymatic hydrolysis: A review, Bioresource Technology, 2010, 101(13), pp. 4851-4861.
Amen-Chen, C. et al., Production of monomelic phenols by thermochemical conversion of biomass: A review, 2001, Bioresource Technology, 2001, 79(3), pp. 277-299.
Berliner, E., Review of book entitled "Electrophilic Substitution in Benzenoid Compounds", Journal of the American Chemical Society, 1966, 88:3, p. 630.
Caporale, L. et al., Characterization of Synthetic Parathyroid Hormone Analogs and of Synthetic Byproducts, The Journal of Organic Chemistry, 1989, 54(2), pp. 343-346.
Carvalheiro, F. et al., Hemicellulose biorefineries: a review on biomass pretreatments, Journal of Scientific & Industrial Research, 2008, 67(11), pp. 849-864.
Chua, M.G.S. et al., Characterization of autohydrolysis aspen (*P. tremuloides*) lignins. Part 3. Infrared and ultraviolet studies of extracted autohydrolysis lignin, Canadian Journal of Chemistry, 1979, vol. 57, pp. 2603-2611.
Cygler, J. et al., Positive Charge Transfer in Mixed Alkane Glasses, The Journal of Physical Chemistry, 1983, 87(3), pp. 455-460.
Durairaj, R.B., Resorcinol: Chemistry, Technology and Applications, 2005, Springer, Berlin, 6 pages.
El Hage, R. et al., Effect of autohydrolysis of *Miscanthus x giganteus* on lignin structure and organosolv delignification, Bioresource Technology, 2010, 101, pp. 9321-9329.
Harkin, J.M., Recent Developments in Lignin Chemistry, in: Topics in Current Chemistry, 1966, vol. 6, Springer Berlin / Heidelberg, pp. 101-158.
Hocking, M.B., Vanillin: Synthetic Flavoring from Spent Sulfite Liquor, Journal of Chemical Education, Sep. 1997, 74 (9), pp. 1055-1059.
Kim, Y. et al., Soluble inhibitors/deactivators of cellulase enzymes from lignocellulosic biomass. Enzyme and Microbial Technology, 2011, 48(4-5), pp. 408-415.
Kubo, S. et al., Lignin-Based Polymer Blends and Biocomposite Materials, in: Natural Fibers, Biopolymers, and Biocomposites, CRC Press, 2005, 27 pages.
Larsson, S. et al., The generation of fermentation inhibitors during dilute acid hydrolysis of softwood, Enzyme and Microbial Technology, 1999, 24(3-4), pp. 151-159.
Li, J. et al., Lignin depolymerization/repolymerization and its critical role for delignification of aspen wood by steam explosion, Bioresource Technology, 2007, 98(16), pp. 3061-3068.
Li, J. et al., Improved lignin properties and reactivity by modifications in the autohydrolysis process of aspen wood, Industrial Crops and Products, 2008, 27(2), pp. 175-181.
Lora, J.H. et al., Autohydrolysis-extraction: a new approach to sulfur-free pulping, Tappi, 1978; 61(12): pp. 88-89.

(Continued)

*Primary Examiner* — Peter F Godenschwager
(74) *Attorney, Agent, or Firm* — The Webb Law Firm

(57) ABSTRACT

The disclosure describes a process for the production of a cellulosic feedstock for enzymatic hydrolysis and/or a lignin fraction for chemicals production, characterized in that a) the raw material is lignocellulosic biomass b) the biomass is treated in hot water c) at least one carbonium ion scavenger is present in the treatment.

24 Claims, 5 Drawing Sheets

(56) References Cited

OTHER PUBLICATIONS

Lora, J. H. et al., Simulated Autohydrolysis of Aspen Milled Wood Lignin in the Presence of Aromatic Additives. Changes in Molecular Weight Distribution, Journal of Applied Polymer Science, 1980, 25(4), pp. 589-596.

Lynd, L.R. et al., How biotech can transform biofuels, Nature Biotechnology, Feb. 2008, 26(2), pp. 169-172.

Mosier, N. et al., Features of promising technologies for pretreatment of lignocellulosic biomass, Bioresource Technology, 2005, 96(6), pp. 673-686.

Overend, R.P. et al., Fractionation of Lignocellulosics by Steam-Aqueous Pretreatments [and Discussion], Philosophical Transactions of the Royal Society of London, Series A, Mathematical and Physical Sciences, 1987, 321 (1561), pp. 523-536.

Pan, X. et al., Strategies to Enhance the Enzymatic Hydrolysis of Pretreated Softwood with High Residual Lignin Content, Applied Biochemistry and Biotechnology, 2005, 124(1), pp. 1069-1079.

Pielhop, T. et al., Two-step approach for the conversion of kraft lignin into aromatic chemicals using acidic oxidation followed by hydrogenolysis, The third Nordic Wood Biorefinery Conference NWBC 2011, Stockholm, pp. 194-199.

Radt, F., Elsevier's Encyclopedia of Organic Chemistry, Series III, vol. 12B, 1950, Elsevier, New York, pp. 1210-1249.

Rahikainen, J. et al., Lignin isolation and characterisation for cellulase adsorption and inhibition studies, in: 12th European workshop on lignocellulosics and pulp, 2012, Espoo, Finland.

Ramos, L.P. et al., Effect of enzymatic hydrolysis on the morphology and fine structure of pretreated cellulosic residues, Enzyme and Microbial Technology, 1993, 15(10), pp. 821-831.

Richter, G., Some Questions Concerning Composition and Behavior at Dissolving-Type Celluloses, 1956, Tappi, 39 (9), pp. 668-672.

Rudolf Van Rohr, P. et al., Lignin To Phenols (LIGTOP) proposal, submitted and approved by CTI, 2005, Bern, Switzerland, 16 pages.

Studer, M.H. et al., Engineering of a High-Throughput Screening System to Identify Cellulosic Biomass, Pretreatments, and Enzyme Formulations That Enhance Sugar Release, Biotechnology and Bioengineering, 2010, 105 (2), pp. 231-238.

Studer, M.N. et al., Lignin content in natural Populus variants affects sugar release, Proceedings of the National Academy of Sciences, 2011, 108(15), pp. 6300-6305.

Sudo, K. et al., Enzymatic Hydrolysis of Woods—Part IX. Catalyzed Steam Explosion of Softwood, Holzforschung, 1986, 40(6), pp. 339-345.

Voitl, T. et al., Oxidation of Lignin Using Aqueous Polyoxometalates in the Presence of Alcohols, ChemSusChem, 2008, 1(8-9), pp. 763-769.

Voitl, T. et al., Analysis of products from the oxidation of technical lignins by oxygen and $H_3PMo_{12}O_{40}$ in water and aqueous methanol by size-exclusion chromatography, Holzforschung, 2010, 64(1), pp. 13-19.

Voitl, T. et al., Demonstration of a Process for the Conversion of Kraft Lignin into Vanillin and Methyl Vanillate by Acidic Oxidation in Aqueous Methanol, Industrial & Engineering Chemistry Research, 2010, 49(2), pp. 520-525.

Wayman, M. et al., Aspen autohydrolysis—The effects of 2-naphtol and other aromatic compounds, Tappi, 1978, 61 (6), pp. 55-57.

Werhan, H. et al., Acidic oxidation of kraft lignin into aromatic monomers catalyzed by transition metal salts, Holzforschung, 2011, 65, 7 pages.

Wollrab, A., Organische Chemie—Eine Einfuhrung fur Lehramts— und Nebenfachstudenten. 3 ed., 2009, Springer-Verlag, Berlin, English-language Abstract, 2 pages.

Yu, Z. et al., The effect of delignification of forest biomass on enzymatic hydrolysis, Biosource Technology, 2011, vol. 102, pp. 9083-9089.

\* cited by examiner

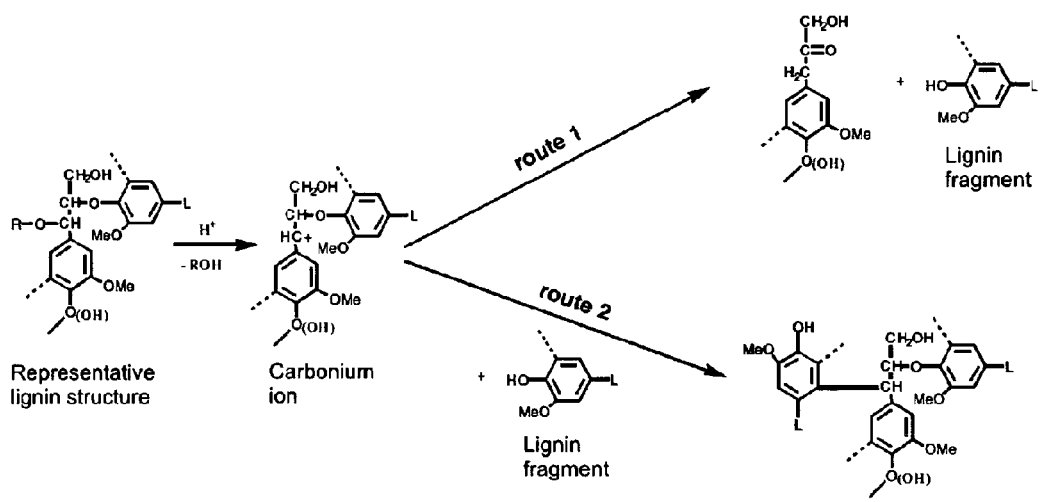
Figure 1 Reaction scheme denoting the competition between depolymerisation of a β-O-4⁻ structure in lignin (route 1) and repolymerisation involving a lignin fragment with a reactive aromatic carbon (route 2) (Li, Henriksson et al., 2007)

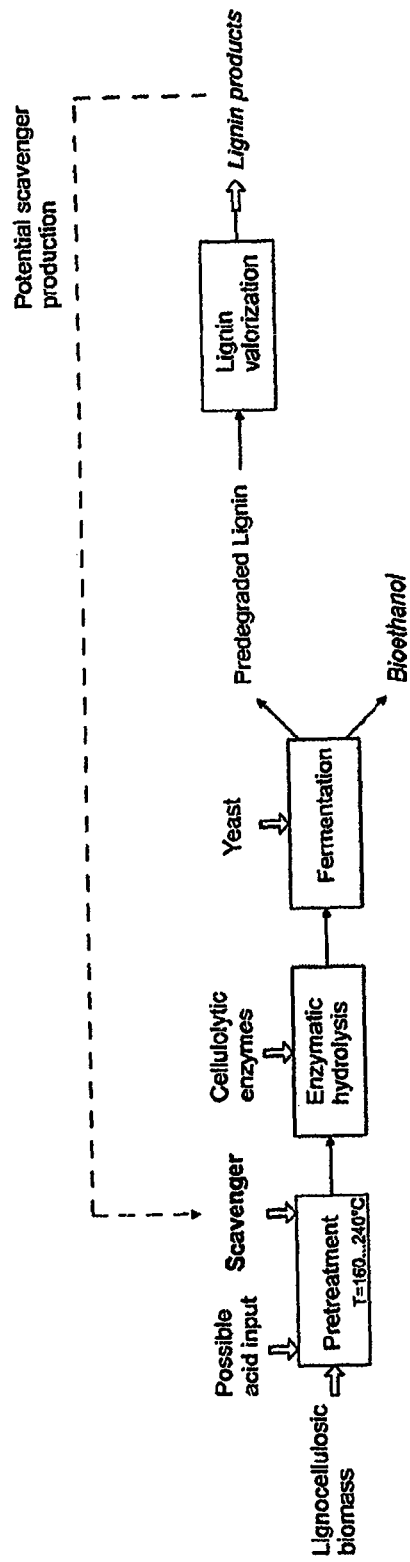
Figure 2 Simplified scheme of a biorefinery employing scavenger during hot water pretreatment

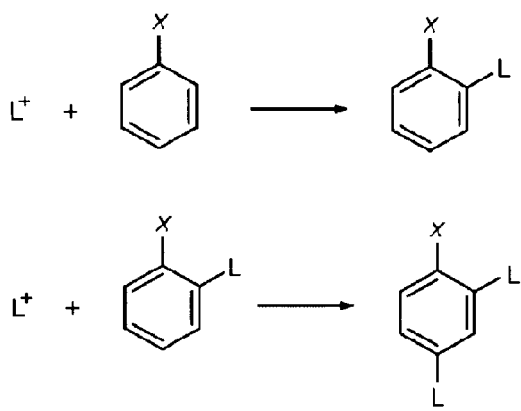
Figure 3 Effectiveness of additive as a blocking agent adapted from (Wayman & Lora, 1978)
Top: scavenging of carbonium ion (L+) by additive. Bottom: recondensation of lignin through additive
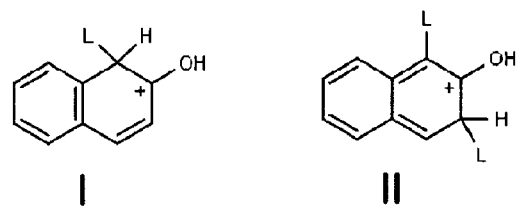
Figure 4 Transition states in the electrophilic substitution of 2-Napthol with a lignin carbonium ion
I: First substitution II: Second substitution

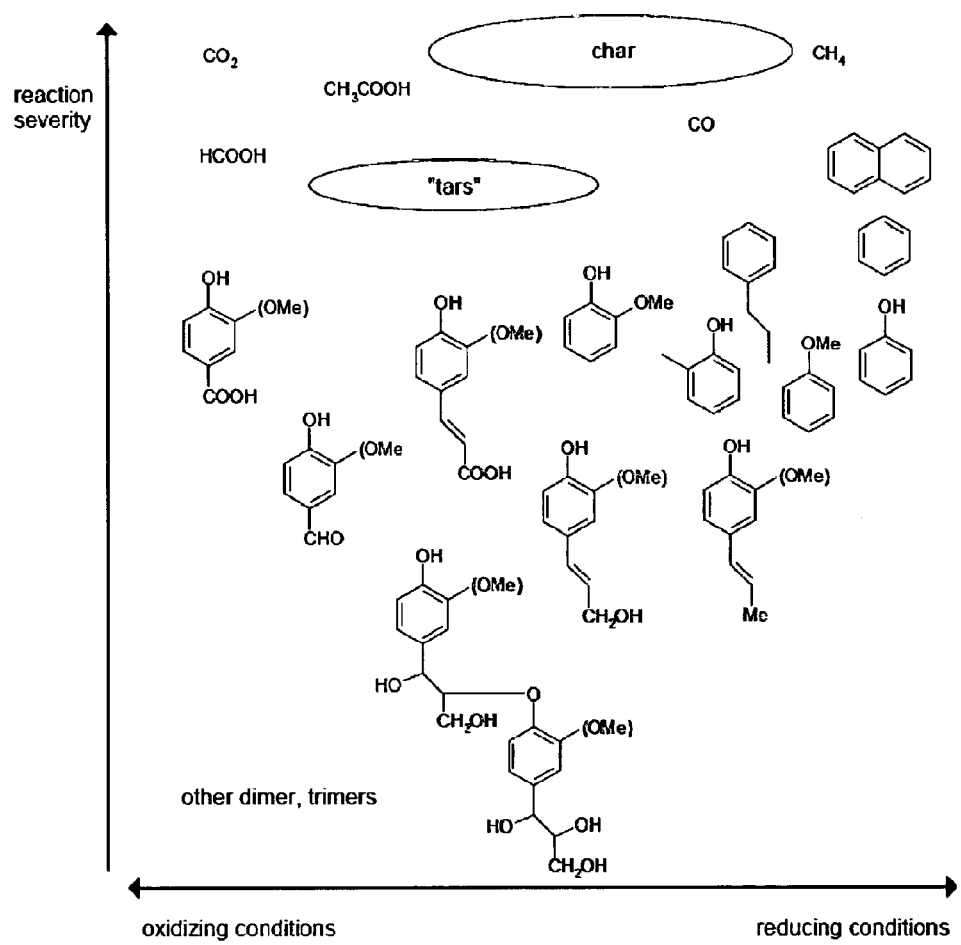
Figure 5 Typical products obtained from lignin depending on oxidizing/reducing character and severity of the reaction adapted from (Rudolf von Rohr, Vogel et al., 2005)

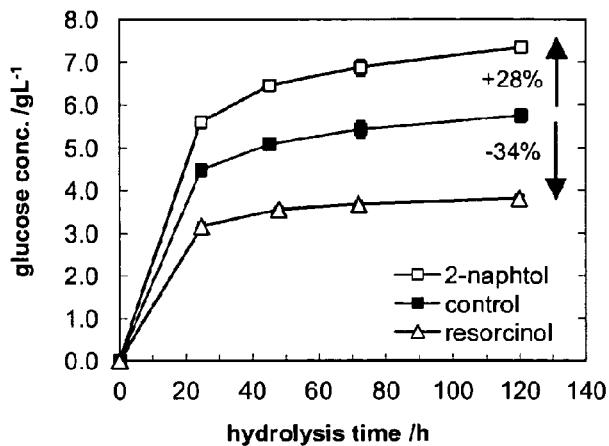

Figure 6 Comparison of glucose formation by enzymatic hydrolysis after 2h hot water treatments with 2-naphtol, resorcinol and without additive (experiments 04, 09 and 14).

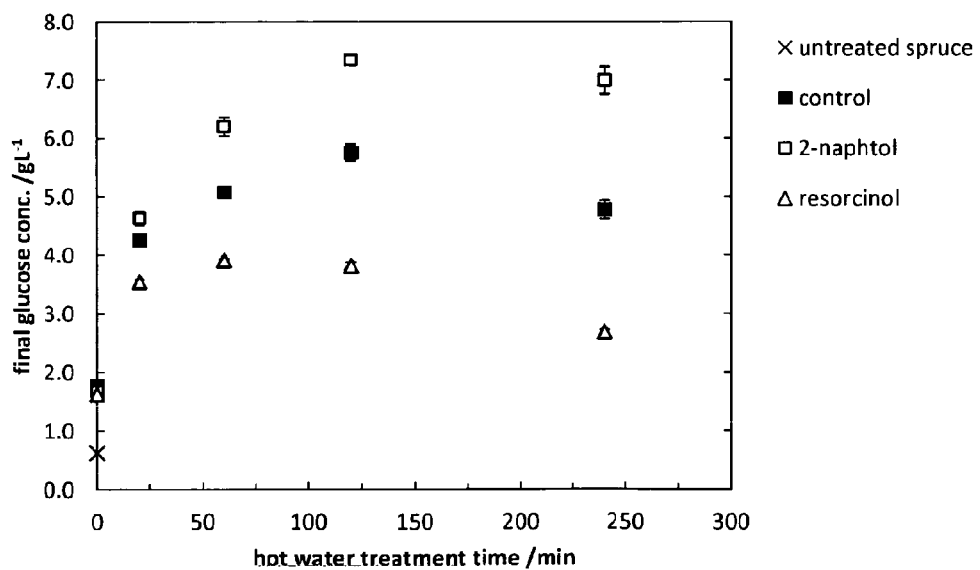

Figure 7 Final glucose concentration formed after 5 days in the enzymatic hydrolysis of biomass hot water treated for varying times with 2-naphtol, resorcinol and without additive (experiments 01 - 15). A treatment time of zero means the reactor was heated to 210°C and instantly cooled down again.

USE OF CARBONIUM ION SCAVENGERS IN THE TREATMENT OF LIGNOCELLULOSIC BIOMASS

CROSS-REFERENCE TO RELATED APPLICATIONS

This application is the United States national phase of International Application No. PCT/EP2012/004599 filed Nov. 5, 2012, and claims priority to European Patent Application No. 11008860.6 filed Nov. 8, 2011, the disclosures of which are hereby incorporated in their entirety by reference.

FIELD OF THE INVENTION

The invention relates to a process using carbonium ion scavengers in the treatment of lignocellulosic biomass for a subsequent production of biofuels and aromatic chemicals.

1. BACKGROUND OF THE INVENTION

Lignocellulosic biomass is the only sustainable resource in terms of cost, availability, and scale that can be converted into liquid fuels to reduce the prevailing role of petroleum in providing energy for the world's transportation needs and to decrease the emissions of fossil-based $CO_2$ that damage the world's climate (Studer & DeMartini et al., 2010). However, physical and chemical barriers caused by the entanglement of the main components of lignocellulosic biomass, hinder the hydrolysis of cellulose and hemicellulose to fermentable sugars (Alvira & Tomás-Pejó et al., 2010). Therefore, pretreatment steps for lignocellulosic biomass aim at breaking down the lignin structure and disrupting the crystallinity of cellulose to enhance enzyme accessibility to the cellulose during the hydrolysis step (Mosier & Wyman et al., 2005). This pretreatment of lignocellulosic biomass is a primary obstacle to a low cost biological processing (Studer et al., 2010), as it represents the second most expensive unit operation (Mosier et al., 2005). The conversion of lignocellulosic biomass to ethanol, butanol or any other liquid fuel will not be competitive until the cost of the sugars from which they are made is lowered significantly (Lynd & Laser et al., 2008). Hence, the development of more effective and economic pretreatments would be of great benefit, especially for softwood with its particular recalcitrance for hydrolysis.

Lignin, the second main component of lignocellulosic biomass after cellulose, is generally regarded as a potential energy source or as feedstock for the production of arenes due to its aromatic structure in prospective biorefinery processes. The potential of lignin as a renewable feedstock for the production of aromatic chemicals is well-known. The recovery of valuable products from lignin is from economical and ecological points of view interesting as phenolics from petro-industry represent high sale volumes and find application in a wide range of industrial processes. The production of fine chemicals (e.g. vanillin) from lignin with lower sale volumes but higher sale prices also possesses large economic and ecological potential. For those reasons, numerous attempts to depolymerise lignin into monomeric chemicals have been studied (Amen-Chen, Pakdel et al., 2001), but the breakthrough for processes that convert lignin into higher value base chemicals is still pending (Voitl, Nagel et al., 2009). While different processes for the production of pulp or chemicals from cellulose have reached industrial scales, economic processes for the production of chemicals from lignin are usually restricted to the production of relatively low cost dispersing or binding agents. There exists only one commercial process that yields reasonably high amounts of a single monomeric product (vanillin) from lignosulfonates in sulfite pulping (Voitl & Rudolf von Rohr, 2010). However, the synthetic formulation of vanillin based on petrochemical routes (via guaiacol) has almost replaced vanillin production based on lignin (Hocking, 1997). The upcoming biorefinery sector offers new opportunities for the valorization of lignin, though.

Summing up, two major drawbacks in the development of profitable biorefineries using a lignocellulosic feedstock are the lack of low capital intensive and environmentally superior pretreatment processes and an unsettled value creation of the lignin. Both issues are addressed in one step in the present invention.

Most of the approaches of lignin exploitation deal with specific lignins arising as a by- or wasteproduct from certain processes in pulping or pretreatment fractionation, that have already been chemically modified. The value creation of lignin is just started to be considered at the end of the pulping. On the other hand, pretreatments for biofuel production from lignocellulosic biomass basically aim at modifying the lignin fraction for an improved enzymatic hydrolysis but not on lignin exploitation. The invention describes an integrative approach, allowing for the valorisation of cellulose and lignin. The valorisation of both fractions is implemented from the beginning, which means already at the pretreatment of lignocellulosic biomass.

The invention describes the use of scavengers for carbonium ions that are formed in the hot water treatment of lignocellulosic biomass, which can both enhance delignification to produce a highly digestible (ligno)cellulose for enzymatic hydrolysis and allow the production of a well-defined pre-depolymerised lignin fraction to be exploited in a further reaction step.

PRIOR ART

Key Factors for an Effective Pretreatment

Biomass pretreatment is a crucial step in the biotechnological conversion of lignocellulosic material to biofuels. Existing pretreatment technologies cover biological, mechanical, chemical and physico-chemical pretreatments. The main goal of the pretreatment for an efficient biofuel production process based on enzymatic hydrolysis is to increase the enzyme accessibility of cellulose and thereby improving its digestibility. High yields of fermentable cellulosic and hemicellulosic sugars should be allowed for by the pretreatment step. This also means that no sugar degradation should take place in the pretreatment. Furthermore, a minimum of toxic products should be generated, which potentially hinder the enzymatic hydrolysis of cellulose as well as the subsequent fermentation to ethanol (Larsson & Palmqvist et al., 1999). Harsh pretreatment conditions (e.g. temperatures >190° C.) lead to a partial degradation of hemicellulosic sugars and the generation of toxic compounds (e.g. furfural, hydroxymethylfurfural). Lignin degradation can lead to the formation of inhibitory and deactivating phenolic compounds, too (Kim & Ximenes et al., 2011).

In the pretreatment, lignin should be recovered to simplify downstream processing and for the conversion into valuable co-products (Alvira et al., 2010). Lignin is also one of the major barriers for enzymatic hydrolysis, which makes lignin processing even more important. In native biomass, one function of lignin is to protect cellulose against microbial or chemical degradation and thus, it represents a hindrance for enzymatic hydrolysis, too. Besides that, lignin counterproductively adsorbs enzymes in the enzymatic hydrolysis step. Therefore, the removal of lignin not only exposes more accessible cellulose by creating pores and breaking the lignin-carbohydrate complex, but also reduces strong surface interaction between lignin and enzymes (Yu & Jameel et al., 2011).

Hot Water Pretreatment

Hot water pretreatment uses hot water at elevated temperatures to provoke alterations in the structure of lignocellulose. The slurry generated after pretreatment can be filtered to obtain two fractions: a solid cellulose-enriched fraction and a liquid fraction rich in hemicellulose derived sugars (Alvira et al., 2010). No external acids or chemicals are needed, as organic acids like acetic acid are generated from hemicellulose (autohydrolysis) leading to a pH between 3 and 5. Equipment corrosion problems are reduced and acid recycling and precipitates removal is no longer necessary like in (concentrated) acid pretreatments. Besides that, in concentrated acid, sugars from hemicellulose are more easily degraded to aldehydes like furfural, which are inhibitory to microbial fermentation. As a result of the milder pH in hot water pretreatment, less inhibitors are formed and less sugar is degraded (Mosier et al., 2005). Typical temperatures for hot water pretreatment range from about 160° C. to 240° C. Below 100° C., there is no hydrolysis effect on the material, whereas above 240° C. pyrolysis reactions become important (Carvalheiro, Duarte et al., 2008).

Lignin Depolymerisation/Repolymerisation

Many authors have established that under various acidic treatments of wood (such as hot water treatment) carbonium ions are formed in different positions of the lignin molecule (Wayman & Lora, 1978). The acid conditions lead to the formation of a carbonium ion by the proton induced elimination of water from the benzylic position in lignin. These carbonium ions have been identified as intermediates in depolymerisation reactions, especially in the breaking of β-arylether linkages. On the other hand the electrophilic carbonium ions are also able to form, through substitution, C—C bonds with the electron rich carbon atoms of the aromatic rings present in lignin as shown in FIG. 1. High-molecular weight, highly condensed and insoluble structures are formed (Wayman & Lora, 1978).

During hot water treatment lignin is partially depolymerised and thereby solubilised, but a complete delignification is not possible using hot water alone. Among other factors, this is due to the repolymerisation of soluble components originating from lignin (Alvira et al., 2010). Those depolymerisation/repolymerisation reactions also lead to an increase in the heterogeneity of the resulting lignin (Li et al., 2007), making it less attractive for a further processing.

A well-known approach for the suppression of undesired repolymerisation is the use of scavengers that can suppress repolymerisation reactions. This approach also showed to be very beneficial in the delignification of lignocellulosic biomass when aromatic compounds acted as scavengers for the carbonium ions (Li et al., 2007; Wayman & Lora, 1978). The aromatic compounds are able to react with electrophilic substances and compete with the aromatic rings present in lignin for the formed carbonium ions. Especially compounds with fused aromatic rings like 2-naphtol are very active towards the electrophilic substitution (Wayman & Lora, 1978). It is possible to achieve a large yield of organic solvent extractable lignin at autohydrolysis temperatures substantially lower than those required without additives. As stated before, a lower temperature in the pretreatment step can prevent the formation of fermentation inhibiting substances like furfurals. Furthermore, the suppression of lignin repolymerisation reactions yields a more uniform and easily extractable lignin of lower molecular weight. Such a lignin is assumed to have a much higher chemical value than the heterogeneous lignin being formed in other pretreatment or pulping processes (Li et al., 2007).

Another approach to prevent lignin recondensation in autohydrolysis, is the addition of alkali salts to neutralize the acids set free during the hot water treatment. As acidic conditions lead to the formation of the carbonium ions, less repolymerisation reactions can be expected as reported by Li and Gellerstedt (2008) in aspen autohydrolysis with small amounts of sodium hydroxide. The obtained lignin shows a lower degree of condensation and a more defined molecular weight distribution compared to the control. However, since the depolymerisation of lignin is also acid catalysed, a poorer delignification of the biomass is reached compared to the hot water treatment with a scavenger (2-naphtol) instead of neutralization.

Scavengers are also employed in the acidic depolymerisation of technical lignins. Depolymerization of lignin proceeding via acidic oxidation is known from literature to cause condensation of lignin fragments, ending up with carbonaceous material instead of monomeric depolymerization products (Bodo & Muirhead et al., 1966). An approach for the acidic oxidation of kraft lignin uses methanol as co-solvent or carbonium ion scavenger to inhibit those condensation reactions in acidic media and the effect was successfully demonstrated (Voitl & Rudolf von Rohr, 2008). Vanillin and methyl vanillate are produced from lignin by the acidic oxidation at 170° C., methyl vanillate is thereby formed by the esterification of vanillic acid with the methanol of the solvent (Voitl & Rudolf von Rohr, 2010). In general, simple alcohols like methanol or ethanol can prevent the acid induced condensation of lignin and substantially improve monomer yields and the depolymerisation of lignin. The average molecular weight of lignin can be decreased from 3500 g/mol (kraft lignin) down to 500 g/mol (Werhan & Mir et al., 2011). The oxidation in acidic aqueous methanol (80% w/w) leads to the complete dissolution of the obtained lignin oxidation products without any char formation—usually a common problem in lignin conversion.

2. DESCRIPTION OF THE INVENTION

2.1 Originality of the Invention

The concept of the invention differs substantially from previous approaches. The invention aims at combining the pretreatment of lignocellulosic biomass for biofuels production with the production of aromatic chemicals from lignin by using carbonium ion scavengers in the pretreatment step.

As described above, carbonium ion scavengers have already successfully been employed in the production of chemicals from technical lignins under acidic conditions and temperatures similar to temperatures in pretreatment. Carbonium ion scavengers used in hot water treatment (defined in this document as a treatment using hot water, steam or both) of wood can also prevent repolymerisation reactions in lignin depolymerisation. Using this pre-depolymerised lignin can improve the production of monomers from lignin in a second reaction step, as less C—C bonds have been formed and a major part of the lignin bonds have already been cleaved. In addition to that, the obtained lignin will have a more homogeneous form simplifying a further processing.

The enhanced delignification in the hot water treatment using carbonium ion scavengers can increase enzyme accessibility and improve the digestibility of cellulose, as confirmed in several experiments (FIG. 7). Experiments described in literature using carbonium ion scavengers in the pretreatment of wood are constrained to the production of pulp for the pulp & paper industry or to the simple delignification of wood. No process or experiment is described in literature using carbonium ion scavengers in the hot water treatment of lignocellulosic biomass in order to improve the enzymatic hydrolysis of the cellulose fraction, preferential for a subsequent biofuels production. The enzymatic hydrolysis of cellulose is a process highly sensitive towards the addition of chemicals (e.g. through enzyme inhibition), making a deliberate scavenger selection and processing necessary.

As an innovation, the present approach aims at a concurrent exploitation of cellulose and lignin that is already implemented in the pretreatment step of a biorefinery process. Synergetic effects result from the simultaneous valorisation of both fractions in this integrative approach. An enhanced delignification of the cellulose fraction comes along with the production of a high quality lignin fraction at the same time. The potential of such a lignin fraction—a lignin with a low, more defined molecular mass and less repolymerisation—for further processing is high. The evaluation of alternative production routes for aromatic chemicals (e.g. vanillin) and other products becomes possible.

As a distinctive feature, the process also includes the option of a scavenger production from the obtained lignin in the process itself. The sustainability of the process is integrated in that way, as it takes into account the reproducibility of the used chemicals. Scavengers like 2-Naphthol, that already proved effective in experiments (FIG. 7), are petrol-based phenols. If those scavengers cannot be supplied from renewable resources, they can however be regarded as a model for other, reproducible additives in the long term.

The main objects of the present invention can be summarized to the following points:
  Enhance the enzymatic digestibility of cellulose by the use of carbonium ion scavengers in the hot water treatment of lignocellulosic biomass
  Production of a homogeneous and uncondensed lignin fraction for a subsequent chemicals production
  Provide a simultaneous valorization of cellulose and lignin in an integral pretreatment approach
  Option of a scavenger production in the process from lignin itself
  Provide a low cost and environmentally superior pretreatment process 2.2 Detailed Description of the Process Steps The invention covers the three basic areas of a typical biorefinery: pretreatment, hydrolysis & fermentation and lignin valorisation, which are closely related to each other (FIG. 2).

2.2.1 Hot Water Treatment

The hot water treatment is the first step in this invention. A scavenger has to be used, which is effective for delignification regarding a subsequent saccharification. Preferably, it results in a favourable lignin depolymerisation regarding final lignin products.

Scavengers

Aromatic organic compounds have already been used in hot water pretreatment to increase the organic solvent extractability of lignin after pretreatment (Lora & Wayman, 1980; Wayman & Lora, 1978). A patent (U.S. Pat. No. 6,770,168 B1) describes the use of organic compounds as catalysts or compounds to prevent self-condensation of lignin in the pretreatment for an oxygen delignification process. The process exclusively follows the aim of liberating the pulp from disturbing lignin but without valorizing the latter. The possibility of treating the lignin with appropriate scavengers for the production of chemicals from the resulting lignin has not been considered yet. In particular, the process aims at removing the lignin for the production of a paper grade pulp. The use of scavengers for improving the cellulose digestibility for enzymatic hydrolysis has not been taken into account in any publication. Improving the enzymatic accessibility of lignocellulosic biomass by hot water treatments does not necessarily mean the lignin has to be removed before hydrolysis, but can also be achieved by a favourably alteration of the lignin structure. This is shown in experiments where the use of a scavenger in hot water treatments increased biomass digestibility without removing more lignin than standard hot water treatments (see section 3 and table 2). Moreover, the enzymatic hydrolysis calls for a special scavenger selection and/or processing, since it is very sensitive towards the addition of chemicals. The present invention in particular implements the use of carbonium ion scavengers in the hot water treatment.

Scavengers which couple with the carbonium ions formed in lignin have to be nucleophilic substances that can compete with the aromatic rings present in lignin for the carbonium ions. As stated earlier, several aromatic compounds have proved to act beneficial as carbonium ion scavengers for lignin fragments, especially compounds with fused aromatic rings are active towards an electrophilic substitution (Wayman & Lora, 1978). Polycyclic aromatics have a high electron density in the ring system and the activation energy of the initial step in the electrophilic process is lower than e.g. for phenol (Li et al., 2007). Depending on their substituents, aromatic compounds can also exhibit certain positions with an increased electron density dedicated for an electrophilic substitution. Blocking agents to be especially considered are compounds with the ability to undergo a single substitution (Wayman & Lora, 1978). If the additive can undergo several subsequent substitutions, it will not act as a blocking agent, but in contrary support the repolymerisation of lignin fragments as illustrated in FIG. 3.

In order to describe how additives can act as a blocking or as a crossing agent, it is convenient to consider the possible transition states that are formed in an electrophilic substitution. The action of a scavenger as a blocking agent will be described in the following exemplary with 2-naphtol, which already proved as a very effective scavenger in hot water treatment for a later enzymatic hydrolysis (FIG. 7). The mechanisms proposed here represent the present state of knowledge and are not to be interpreted as a restriction of the invention. 2-naphtol is easily substituted in position 1 (Radt, 1950) due to the ortho-directing hydroxy group (compare FIG. 4, compound I). The positive mesomeric effect (+M-effect) of the hydroxy group adds to the stabilisation of the positive charge in the transition state. Note that the transition state structure is still of a benzoid type. In a possible second electrophilic substitution a carbonium ion could then attack at position 3, with the positive charge of the transition state again being stabilised by the hydroxy group (compare FIG. 4, compound II). However, the benzoid type is not preserved in the corresponding structure. As benzoid structures can be regarded as energetically favourable and stable in the electrophilic substitution of polycyclic aromatics (Wollrab, 2009), this second substitution does not occur easily. 2-naphtol acts therefore as a blocking agent, but not as a crossing agent.

Effective scavengers used in the process can be solid, liquid or gaseous compounds. Preferably aromatic compounds that undergo electrophilic substitutions and especially compounds that undergo just a single electrophilic substitution are to be considered. Those can include substituted monocyclic (e.g. phenol, anisol, guaiacol, hydrobenzoic acids, cresols xylenols, catechols) and polycyclic aromatics (e.g. 2-naphtol). Also non-substituted polycyclic aromatics (e.g. naphthalene, pyrene) can be effective, as polycyclic aromatics with their high electron density are very active towards electrophilic substitutions (Norman & Taylor, 1965). Especially profitable are compounds that can be produced from the lignin generated in the process itself, like for example guaiacols, o/m-cresol, benzene, naphthalene, pyrene or p-hydrobenzoic acid. Simple alcohols like methanol or ethanol can also act as carbonium scavengers and can be produced in the process itself from cellulose. It is also possible to employ mixtures of different scavengers.

Parameters in Hot Water Treatment

Any lignocellulosic material containing fermentable carbohydrate (e.g. softwood, hardwood, herbaceous biomass, agricultural residues) with an open structure can serve as raw material for the hot water treatment. Sawdust and wood flour as well as wood splinters and slivers can also be used in accordance with the present invention without any preceding chipping or destructuration. Preferred raw materials are softwoods such as spruce, pine or larch and hardwoods such as beech, birch or eucalyptus. Softwood is considered particularly recalcitrant for hydrolysis owing to the higher amount and nature of lignin (Pan & Xie et al., 2005) and an effective pretreatment overcoming this resistance is therefore especially favourable for this kind of lignocellulose.

An autohydrolysis process as presented in this invention is favourably in this perception, as softwood lignins are more affected by this treatment and undergo more delignification than hardwood lignins (Chua & Wayman, 1979; Richter, 1956). Consequently, a greater effect of the hot water treatment on the subsequent enzymatic hydrolysis can result for softwoods. The delignification itself is also more important for softwood than for hardwood in enzymatic hydrolysis. Softwood lignin contains mainly guaiacyl units, while hardwood lignin contains mixed guaiacyl and syringyl units, and it was observed that guaiacyl lignin restricts fiber swelling and enzymatic accessibility more than syringyl lignin (Ramos, Nazhad et al., 1993). It was reported that the carbohydrate conversion by action of enzymes after hot water pretreatment is generally higher with a higher syrigyl/guaiacyl (S/G) ratio (Studer & DeMartini et al., 2011). Condensation reactions also take place more easily in the guiacyl moiety than in the syringyl moiety (Sudo & Shimizu et al., 1986), so that the scavenging of carbonium ions in hot water treatment is more important for softwoods, too. The differences in structure also mean that the lignin composition of softwood is less variable than that of hardwood and can therefore represent a better starting material for the later production of single chemicals in high yields from lignin. Nevertheless, the proposed process can also prove beneficial for hardwood types of wood and any other lignocellulosic resources.

The lignocellulosic material can be treated as a suspension in a liquid phase and/or directly with steam. Steam treatment methods are preferred, as they allow for high solids concentration as favoured in commercial operations. Depending on the reactor system used, the water to dry biomass ratio could be in the range between 1:1 and 100:1. Preferred reactor types for the hot water treatment are (stirred) tank or steam (explosion) reactors that can be operated in batch or continuous mode. Other possible types of reactors include for example tubular reactors or reactors where lignocellulosic material is packed in a slowly moving bed and the fluid or steam may be in either concurrent or countercurrent flow.

The scavenger can be added for example by direct addition to the liquid phase in liquid hot water treatment or impregnation of the biomass prior to hot water treatment. The quantity of the scavenger added in the hot water treatment may vary in a wide range between 0.01 to 10% w/w based on dry biomass loading. An optimum scavenger loading in the hot water treatment aims at a good delignification of the biomass and a complete conversion of the scavenger. A complete conversion means that there is no need for a scavenger recycling and a possible inhibition of the enzymatic hydrolysis or fermentation by the scavenger can be excluded. An effective scavenger will allow for a reduction of severity in the hot water treatment, i.e. temperature and time. This can be beneficial for hydrolysis and fermentation performances, as less toxic degradation products are formed. Operation of the hot water treatment at lower temperatures can be possible if the self-condensation reactions of lignin are prevented or slowed (Wayman & Lora, 1978), as intended by the scavenger. It can be expected that the use of effective scavengers also allows for a faster delignification rate of the biomass, as reported in (Wayman & Lora, 1978).

The hot water treatment can be carried out for example under an atmosphere consisting or containing an inert gas, oxygen, ozone, $CO_2$ or hydrogen, preferably under inert gas or air. The temperature in the hot water treatment step is maintained within the range from about 100 to 260° C., preferably from about 190 to 240° C. The duration of the treatment can vary from one minute to several days as long as the particle structure is thoroughly penetrated. At higher temperatures, a shorter treatment time is required. For example a retention time of 3 to 60 minutes can suffice at 190 to 240° C., while 60 minutes to several hours may be necessary to obtain the desired result at precooking temperatures lower than about 190° C. It is also possible to carry out a multi-step treatment. For example a mild treatment stage at lower temperatures (or short treatment times) followed by a harsher treatment stage at higher temperatures (or longer treatment times). In that way, dissolved hemicellulosic sugars can be recovered after the first treatment stage. The separated biomass then can undergo a harsher treatment for improving the cellulose digestibility including the use of scavengers for preventing lignin condensation reactions, which especially occur at harsh treatments.

The pH during hot water treatment preferably lies in the range between about 2 and 4 due to the release of organic acids from the biomass, however the pH can be lowered further by the addition of acids. Inorganic acids such as nitric acid, hydrochloric acid or phosphoric acids and organic acids such as acetic or formic acids may be added.

In the hot water treatment step, biomass with a highly digestible cellulose and preferably a high quality, pre-depolymerised lignin are to be produced. The biomass is to be pretreated as well as possible, however without decomposing the desired products or producing a lot of toxic compounds for enzymatic hydrolysis and fermentation. Therefore, this approach represents an optimisation task regarding suitable carbonium ion scavengers, temperature, time etc.

2.2.2 Enzymatic Hydrolysis and Fermentation

The objective for hydrolysis is a high digestibility of the cellulose, i.e. a high sugar yield and a short residence time, while using small amounts of enzyme.

For the presented invention, the enzymatic hydrolysis of hot water treated spruce sawdust can serve as a benchmark. Several experiments (see FIG. 7) prove the use of a carbonium ion scavenger during hot water treatment feasible for enhancing enzymatic hydrolysis. The glucose yield is increased up to 46.3% after the hot water treatment with 2% w/w (based on raw dry biomass) of 2-napthol compared to the control. These results show that due to a suppression of lignin condensation the enzymatic digestibility of the cellulose is improved.

The inhibition of enzymatic hydrolysis and fermentation through byproducts from hot water treatment (e.g. furfurals) and remaining unreacted scavenger is possible. This can be prevented by washing the biomass prior to hydrolysis. From a process engineering point of view, a process without washing is economically favourable. Therefore, either a complete consumption of the scavenger or the use of a non-toxic scavenger is preferred. A reduction of severity in the hot water treatment, as allowed for by an effective scavenger, can prevent the formation of inhibiting compounds from the biomass.

2.2.3 Lignin Valorisation

The remaining biomass after a complete enzymatic hydrolysis basically consists of lignin. This lignin has already been partially depolymerised as a result of the hot water treatment. As stated earlier, this depolymerisation will even have proceeded further than usual due to the suppression of lignin repolymerisation reactions by the scavenger which can yield a much more uniform and homogeneous lignin structure. Such a lignin fraction, with a low and more defined molecular mass and in particular less condensed C—C bonds, can be assumed to have a much higher chemical value and can prove beneficial for the production of chemicals compared to the heterogeneous lignin being formed in other pretreatment or pulping processes. The production of aromatic monomers from those technical lignins, which often have already undergone several processes for their extraction/separation from cellulosic components, and have also been subjected to repolymerisation to a certain degree, is probably limited. The direct use of a lignin formed in a process with suppressed lignin condensation (hence less C—C bonds) as proposed here, should prove beneficial for the production of monomers. The produced lignins will also be purer and sulphur-free, simplifying further processing. Noteworthy, the used scavengers can be integrated into the structures of the later produced chemicals.

Yet in this last step of lignin processing (e.g. lignin oxidation, hydrogenation, hydrogenolysis or pyrolysis), repolymerisation reactions of the lignin can be prevented in order to avoid/minimize the formation of char. This can be done by using scavengers like for example methanol or ethanol (which could be directly supplied from bioethanol production) and have already proved effective in lignin depolymerisation (Voitl & Rudolf von Rohr, 2008).

A cost effective scavenger in the hot water treatment has to be inexpensive or better, is generated within the process. An interesting option is the production of aromatic compounds from the pre-depolymerised lignin that could be used as carbonium ion scavengers for delignification in the initial hot water treatment step. A part of the lignin products are recycled to the hot water treatment stage (FIG. 2), allowing for a treatment process without the need of external chemicals. Generally, a challenge in the production of chemicals from lignin is that complex product mixtures are obtained. However, when using the lignin products as a scavenger mixture for hot water treatment, this is less problematic. As an example, the high-temperature hydrogenolysis or pyrolysis of lignin yields substances with fused aromatic rings (e.g. naphthalenes, pyrenes) (Pielhop, Werhan et al., 2011). Those polyaromatics are probably formed by the coupling of monomer radicals formed at such high temperatures. Polycyclic aromatics are very active in the electrophilic substitution scavenging reactions (Wayman & Lora, 1978) and substances like pyrene have been reported as cation scavengers (Cygler, Teather et al., 1983). Also cresols, which are formed at lower hydrogenolysis temperatures from lignin, can be used as carbonium ion scavengers (Caporale & Nutt et al., 1989). In particular, specific aromatic substance classes can turn out to be effective in the hot water treatment and it can be possible to selectively produce them from lignin. Different products can be produced from lignin depending on the oxidizing/reducing character and the severity of the reaction, as illustrated in FIG. 5.

The produced lignin is also attractive from a polymer chemistry point of view, for use as a component in phenol-based polymers. Available commercial lignins have limited utility in applications which demand a constant well-defined feedstock, due to inherent chemical and molecular weight inhomogeneity (Satoshi, Richard et al., 2005). In the proposed process, lignins with a low, more defined molecular mass and good solubility can be produced. Together with the efficient incorporation of aromatic scavengers into the lignin leading to a high number of corresponding phenolic sites, this should make such lignins attractive as a component for phenol-based polymers (Li & Gellerstedt, 2008).

3. WORKING EXAMPLES

In the following, the presented invention will be explained with the help of representative experiments. In particular, the effectiveness of carbonium ion scavengers in hot water treatment for an improved digestibility of the resulting cellulose is demonstrated. Compared to a state of the art hot water treatment, the digestibility of the cellulose can be improved.

Experimental

Sawdust from excoriated spruce, grown in Solothurn, Switzerland, with a dry matter content of 73.11±0.49% was used as feedstock. The biomass was knife-milled to a particle size <1 mm (Retsch Cutting Mill SM 200) and then sieved to a particle size between 0.18 and 1 mm.

Hot water treatments were conducted in a 100 ml stirred batch reactor (Compact Micro Reactor 5500, Parr Instrument Company, Illinois, USA) equipped with a blade impeller and a cooling finger. The experiments were performed with 2.5 g of spruce in 39.2 g $H_2O$, corresponding to a biomass loading of 6% w/w. Optionally, 50 mg of 2-naphtol (corresponding to 2% w/w of the raw biomass or 0.105 mol/lignin $C_9$ unit) or 38.2 mg of resorcinol (corresponding to 1.53% w/w of the raw biomass or 0.105 mol/lignin $C_9$ unit) were added. The reactor was purged three times with nitrogen (10 bars) to remove oxygen and the stirring rate was set to 500 rpm. The experiments were carried out at 210° C. for varying reaction times. Heating up of the reactor from 100° C. to 210° C. lasted 8 min, cooling down from 210° C. to 100° C. lasted 8 min with the help of pressurised air cooling. The treatment severity, taking into account the heating and cooling process, was estimated as defined by Chornet for hydrothermal pretreatments (Overend, Chornet et al., 1987) to lay between log $R_0$=2.9 and log $R_0$=5.6 (compare table 1). After the hot water treatment, the biomass was filtered, washed three times with 100 ml of cooking water and analysed for its carbohydrate and lignin content.

Enzymatic hydrolysis of the biomass was performed in 10 ml suspensions in 20 ml scintillation vials with a cellulose concentration of 1% w/w. Citric acid buffer (pH 5.0) at a final concentration of 0.05 mol/l, sodium azide at a final concentration of 0.1 g/L and the appropriate amount of enzyme were added. Cellulase (Accellerase 1500; Genencor, Palo Alto, Calif., USA) were added at a final concentration of 0.64 ml/g of cellulose which equals about 60 FPU/g of cellulose. The samples were incubated at 50° C. in a shaking incubator (Multitron 2, Infors-HT, Bottmingen, Switzerland) at 150 rpm for 120 hours.

Glucose and mannose concentrations were analyzed using HPLC. A separation column (Aminex HPX-87H; BioRad, Hercules, Calif., USA) with 0.005 mol/l sulfuric acid as the eluent was used in isocratic mode at 65° C. on a separation module (Alliance 2695; Waters, Milford, Mass., USA) equipped with a refractive index detector (model 2414; Waters) set to 35° C.

In total 15 hot water treatment experiments were carried out (see table 1). Experiments 01-05 were carried out without additive and serve as a benchmark or control experiment. Experiments 06-10 were carried out with 2-naphtol, which acts as a carbonium ion scavenger as described in section 2.2.1. Experiments 11-15 were carried out with resorcinol as additive. Resorcinol can easily undergo more than one electrophilic substitution, increasing the possibility of lignin crossing reactions (Lora & Wayman, 1980). This is due to the positive mesomeric effect (+M-effect) of the two hydroxy groups located at the 1 and 3 positions of the benzene molecule which add to the stabilisation of the positive charge in the transition states (Durairaj, 2005). Therefore, resorcinol acts as a crossing agent and not as a scavenger for lignin fragments and its use in hot water treatment is not reasonable according to the approach of the present invention. However, it is used to further prove the presented reaction concept.

None of the additives seemed to change the pH in hot water treatments compared to the control (see table 1) and their effects are therefore not attributed to a change of pH.

TABLE 1

Overview of hot water treatment experiments

| Experiment | Additive | Hot water treatment time* [min] | Hot water treatment severity $\log R_0$ | pH after hot water treatment |
|---|---|---|---|---|
| 01 | — | 0 | 2.9 | 3.83 |
| 02 | — | 20 | 4.5 | 3.41 |
| 03 | — | 60 | 5.0 | 3.10 |
| 04 | — | 120 | 5.3 | 3.07 |
| 05 | — | 240 | 5.6 | 3.07 |
| 06 | 2-naphtol | 0 | 2.9 | 3.88 |
| 07 | 2-naphtol | 20 | 4.5 | 3.23 |
| 08 | 2-naphtol | 60 | 5.0 | 3.18 |
| 09 | 2-naphtol | 120 | 5.3 | 3.11 |
| 10 | 2-naphtol | 240 | 5.6 | 3.04 |
| 11 | resorcinol | 0 | 2.9 | 3.88 |
| 12 | resorcinol | 20 | 4.5 | 3.23 |
| 13 | resorcinol | 60 | 5.0 | 3.15 |
| 14 | resorcinol | 120 | 5.3 | 3.10 |
| 15 | resorcinol | 240 | 5.6 | 3.12 |

*A treatment time of zero means the reactor was heated to 210° C. and instantly cooled down again.

Effect of Scavengers and Crossing Agents on Biomass Digestibility

FIG. 6 shows the glucose formation in enzymatic hydrolysis after a 2 h hot water treatment of the biomass with 2-naphtol, resorcinol and without additive (experiments 04, 09 and 14). The hot water treatment without additive serves as a benchmark. After the hot-water treatment with 2-napthol, the glucose yield was increased by 27.7%. These results prove the positive action and the effectivity of a carbonium ion scavenger in the hot water treatment. As described previously, 2-naphtol acts as a blocking agent for the carbonium ions formed in lignin in the hot water treatment. In this way, lignin condensation reactions are suppressed and the enzymatic digestibility of the cellulose is improved.

This result is further confirmed by the fact, that the glucose yield was decreased by 33.7% after the hot-water treatment with resorcinol. Resorcinol acts as a crossing agent and favours the repolymerisation of lignin fragments. The increased lignin condensation hinders the enzymatic hydrolysis of the cellulose and thereby decreases the digestibility of the biomass. This negative effect of resorcinol is counterproductive, however it proves the concept of the present invention feasible: suppressing lignin condensation reactions in hot water treatment improves biomass digestibility, increasing lignin condensation reactions worsens biomass digestibility.

Table 2 shows the carbohydrate and lignin content of the biomass before and after the hot water treatments. Characteristic for a hot water treatment, the hemicelluloses (measured here as mannan content) are almost completely removed, whereas cellulose and lignin are hardly dissolved.

Remarkably, the biomasses treated with 2-naphtol and resorcinol have cellulose and lignin contents very similar to the control. This shows that the improved respectively decreased digestibility using those two additives is not based on lignin removal, but rather on a different lignin structure which influences the enzyme accessibility. In this perception, "delignification" not just describes the removal of lignin but rather a favourable breaking down and decomposition of the lignin structure by the suppression of recondensation reactions. This increases the enzymatic digestibility of lignocellulosic biomass without removing the lignin. Probable explanations for this effect are that more condensed lignin structures can block the access of enzymes to cellulose and/or that cellulolytic enzymes stronger adsorb to more condensed lignin structures. An increased adsorption of cellulolytic enzymes on condensed lignin structures has recently been described in (Rahikainen & Heikkinen et al., 2012). It is furthermore imaginable that carbonium ion scavengers can prevent the reaction of sugar degradation products like furfurals with the lignin structure.

The biomass after the hot water treatment with 2-naphtol and resorcinol contains more acid insoluble lignin than the biomass of the control. This can be attributed to the direct incorporation of the additives into the lignin structure. The use of scavengers can therefore also be attractive for introducing functional groups (e.g. phenolic sites) into the lignin for a targeted lignin product formation using tailor-made carbonium ion scavengers.

concept of the present invention: suppressing lignin condensation reactions in hot water treatment improves biomass digestibility, increasing lignin condensation reactions worsens biomass digestibility.

TABLE 2

Composition of the biomass before and after 2 h hot water treatments with 2-naphtol, resorcinol and without additive (experiments 04, 09 and 14)

| Exp. | Description | Cellulose [%] | Mannan [%] | Acid insoluble Lignin [%] | Acid soluble Lignin [%] | Total [%] |
|---|---|---|---|---|---|---|
| — | Untreated Spruce | 45.18 ± 0.55 | 17.74 ± 0.28 | 28.72 ± 0.06 | 4.77 ± 0.42 | 96.14 ± 1.19 |
| 04 | Spruce, hot water treated (control) | 50.96 ± 0.25 | 0.63 ± 1.09 | 46.89 ± 0.09 | 2.35 ± 0.05 | 100.84 ± 0.89 |
| 09 | Spruce, hot water treated (2-naphtol) | 49.56 ± 0.33 | — | 47.97 ± 0.10 | 2.48 ± 0.11 | 100.01 ± 0.42 |
| 14 | Spruce, hot water treated (resorcinol) | 48.58 ± 0.50 | — | 47.74 ± 0.16 | 3.28 ± 0.18 | 99.61 ± 0.44 |

Influence of Hot Water Treatment Time

Varying the hot water treatment time gives more insight into the scavenger mode of action. FIG. 7 shows the final glucose concentration formed after five days in the enzymatic hydrolysis of biomass treated for varying times with and without additive (experiments 01-15).

Remarkably, the glucose concentration of the biomass treated without additive (control) shows a maximum for a treatment time of about 1 h. In the range of 0-1 h, the digestibility of the biomass increases with time due to a harsher treatment and a better disintegration of the wood structure. However, increasing treatment time further leads to a decrease in digestibility. This can probably be explained with the de- and repolymerisation reactions of lignin that take place during treatment. In the beginning of the treatment, the lignin basically undergoes depolymerisation reactions. This depolymerisation however, is followed by a second condensation reaction. With increasing treatment time, more lignin fragments have been formed by the depolymerisation reactions, and the condensation reactions of those fragments become more and more pronounced. For long treatment times >1 h, the condensation reactions apparently lead to a more condensed and repolymerised lignin that constitutes a barrier for enzymatic hydrolysis.

In every experiment using 2-naphtol as a carbonium ion scavenger in hot water treatment, higher glucose concentrations are reached in hydrolysis proving the effectivity of carbonium ion scavengers in the presented approach. The glucose concentration also seems to level off after a certain treatment time. At a treatment time of 4 h, the scavenger could increase the glucose yield by 46.3% compared to the control. The effect of the scavenger gets more pronounced with increasing treatment time, as then the repolymerisation reactions which can be prevented by the scavenger play a major role. The maximum glucose concentration of 7.35 g/l could be obtained for a 2 h hot water treatment using 2-naphtol, corresponding to a cellulose to glucose conversion of 66.8%. Compared to literature data on the enzymatic hydrolysis of softwood, this is an exceptionally high glucose yield after a hot water treatment.

In every experiment using resorcinol as a crossing agent in hot water treatment, lower glucose concentrations are reached in hydrolysis. The decrease in glucose concentration is very similar to the increase caused by 2-naphtol, for instance at a treatment time of 4 h the crossing agent could decrease the glucose yield by 43.9% compared to the control. Again, the negative effect of resorcinol proves the The scientific findings gained in these liquid hot water treatments of lignocellulosic biomass can also be expected to be applicable for steam treatment. The chemical changes introduced in the lignin are very similar (Li & Gellerstedt, 2008) and scavengers effective in hot water treatment like 2-naphtol have also successfully been employed in steam treatment leading to an improved delignification and lignin quality (Li et al., 2007).

It has to be noted, that the examples given in this document represent first experiments. The achievement of the comparatively high yields in cellulose hydrolysis are therefore in particular promising, as the principle according to the invention has not been optimised yet. With regard to the numerous possible combinations of scavengers, biomass type and reaction parameters there is still a lot of room for further improvement.

Besides, several technical modifications in the process are likely to further improve sugar yields. For example a two-stage hot water treatment can be employed with a first mild treatment stage for hemicellulose dissolution. After hemicellulose recovery and separation of the remaining biomass, a second harsher treatment stage including the use of scavengers can be employed for improving cellulose digestibility of the biomass. Another modification in the process could be the addition of external acids. This will increase the effectiveness of the hot water treatment of the biomass for enzymatic hydrolysis. At the same time, the scavenger is likely to be even more effective as carbonium ions in lignin are especially formed under acid conditions.

5. REFERENCES

Alvira, P., Tomás-Pejó, E., Ballesteros, M., Negro, M. J. 2010. Pretreatment technologies for an efficient bioethanol production process based on enzymatic hydrolysis: A review. *Bioresource Technology*, 101(13), 4851-4861.

Amen-Chen, C., Pakdel, H., Roy, C. 2001. Production of monomeric phenols by thermochemical conversion of biomass: a review. *Bioresource Technology*, 79(3), 277-299.

Bodo, G., Muirhead, H., Bohlmann, F., Harkin, J., Gröger, D., Harkin, J. 1966. Recent developments in lignin chemistry. in: *Topics in Current Chemistry*, Vol. 6, Springer Berlin/Heidelberg, pp. 101-158.

Caporale, L., Nutt, R., Levy, J., Smith, J., Arison, B., Bennett, C., Albers-Schonberg, G., Pitzenberger, S., Rosenblatt, M., Hirschmann, R. 1989. Characterization of synthetic parathyroid hormone analogs and of synthetic by-products. *The Journal of Organic Chemistry*, 54(2), 343-346.

Carvalheiro, F., Duarte, L. C., Gírio, F. M. 2008. Hemicellulose biorefineries: a review on biomass pretreatments. *Journal of Scientific & Industrial Research*, 67(11), 849-864.

Chua, M. G. S., Wayman, M. 1979. Characterization of autohydrolysis aspen (*P. tremuloides*) lignins. 1. Composition and molecular weight distribution of extracted autohydrolysis lignin. *Canadian Journal of Chemistry*, 57(10), 1141-1149.

Cygler, J., Teather, G. G., Klassen, N. V. 1983. Positive charge transfer in mixed alkane glasses. *The Journal of Physical Chemistry*, 87(3), 455-460.

Durairaj, R. B. 2005. *Resorcinol: Chemistry, Technology and Applications*. Springer, Berlin.

Hocking, M. B. 1997. Vanillin: Synthetic Flavoring from Spent Sulfite Liquor. *Journal of Chemical Education*, 74(9), 1055-1059.

Kim, Y., Ximenes, E., Mosier, N. S., Ladisch, M. R. 2011. Soluble inhibitors/deactivators of cellulase enzymes from lignocellulosic biomass. *Enzyme and Microbial Technology*, 48(4-5), 408-415.

Larsson, S., Palmqvist, E., Hahn-Hägerdal, B., Tengborg, C., Stenberg, K., Zacchi, G., Nilvebrant, N.-O. 1999. The generation of fermentation inhibitors during dilute acid hydrolysis of softwood. *Enzyme and Microbial Technology*, 24(3-4), 151-159.

Li, J., Gellerstedt, G. 2008. Improved lignin properties and reactivity by modifications in the autohydrolysis process of aspen wood. *Industrial Crops and Products*, 27(2), 175-181.

Li, J., Henriksson, G., Gellerstedt, G. 2007. Lignin depolymerization/repolymerization and its critical role for delignification of aspen wood by steam explosion. *Bioresource Technology*, 98(16), 3061-3068.

Lora, J. H., Wayman, M. 1980. Simulated autohydrolysis of aspen milled wood lignin in the presence of aromatic additives. Changes in molecular weight distribution. *Journal of Applied Polymer Science*, 25(4), 589-596.

Lynd, L. R., Laser, M. S., Bransby, D., Dale, B. E., Davison, B., Hamilton, R., Himmel, M., Keller, M., McMillan, J. D., Sheehan, J., Wyman, C. E. 2008. How biotech can transform biofuels. *Nature Biotechnology*, 26(2), 169-172.

Mosier, N., Wyman, C., Dale, B., Elander, R., Lee, Y. Y., Holtzapple, M., Ladisch, M. 2005. Features of promising technologies for pretreatment of lignocellulosic biomass. *Bioresource Technology*, 96(6), 673-686.

Norman, R. O. C., Taylor, R. 1965. *Electrophilic Substitution in Benzenoid Compounds*. Elsevier, New York.

Overend, R. P., Chornet, E., Gascoigne, J. A. 1987. Fractionation of Lignocellulosics by Steam-Aqueous Pretreatments [and Discussion]. *Philosophical Transactions of the Royal Society of London. Series A, Mathematical and Physical Sciences*, 321(1561), 523-536.

Pan, X., Xie, D., Gilkes, N., Gregg, D., Saddler, J. 2005. Strategies to enhance the enzymatic hydrolysis of pretreated softwood with high residual lignin content. *Applied Biochemistry and Biotechnology*, 124(1), 1069-1079.

Pielhop, T., Werhan, H., Rudolf von Rohr, P. 2011. Two-step approach for the conversion of kraft lignin into aromatic chemicals using acidic oxidation followed by hydrogenolysis. *The third Nordic Wood Biorefinery Conference NWBC 2011*, Stockholm. pp. 194-199.

Radt, F. 1950. in: *Elsevier Encyclopedia of Organic Compounds*, (Ed.) F. Radt, Vol. Series III Volume 12B, Elsevier. N.Y.

Rahikainen, J., Heikkinen, H., Rovio, S., Tamminen, T., Marjamaa, K., Kruus, K. 2012. Lignin isolation and characterisation for cellulase adsorption and inhibition studies. in: *12th European workshop on lignocellulosics and pulp*. Espoo, Finland.

Ramos, L. P., Nazhad, M. M., Saddler, J. N. 1993. Effect of enzymatic hydrolysis on the morphology and fine structure of pretreated cellulosic residues. *Enzyme and Microbial Technology*, 15(10), 821-831.

Richter, G. 1956. Tappi. 39(193).

Rudolf von Rohr, P., Vogel, F., Stark, W. 2005. Lignin To Phenols (LIGTOP) proposal, submitted and approved by CTI. Bern, Switzerland.

Satoshi, K., Richard, G., John, K. 2005. Lignin-Based Polymer Blends and Biocomposite Materials. in: *Natural Fibers, Biopolymers, and Biocomposites*, CRC Press.

Studer, M. H., DeMartini, J. D., Brethauer, S., McKenzie, H. L., Wyman, C. E. 2010. Engineering of a high-throughput screening system to identify cellulosic biomass, pretreatments, and enzyme formulations that enhance sugar release. *Biotechnology and Bioengineering*, 105(2), 231-8.

Studer, M. H., DeMartini, J. D., Davis, M. F., Sykes, R. W., Davison, B., Keller, M., Tuskan, G. A., Wyman, C. E. 2011. Lignin content in natural Populus variants affects sugar release. *Proceedings of the National Academy of Sciences*, 108(15), 6300-6305.

Sudo, K., Shimizu, K., Ishii, T., Fujii, T., Nagasawa, S. 1986. Enzymatic Hydrolysis of Woods—Part IX. Catalyzed Steam Explosion of Softwood. *Holzforschung*, 40(6), 339-345.

Voitl, T., Nagel, M. V., Rudolf von Rohr, P. 2009. Analysis of products from the oxidation of technical lignins by oxygen and H3PMo12O40 in water and aqueous methanol by size-exclusion chromatography. *Holzforschung*, 64(1), 13-19.

Voitl, T., Rudolf von Rohr, P. 2010. Demonstration of a Process for the Conversion of Kraft Lignin into Vanillin and Methyl Vanillate by Acidic Oxidation in Aqueous Methanol. *Industrial & Engineering Chemistry Research*, 49(2), 520-525.

Voitl, T., Rudolf von Rohr, P. 2008. Method for the Breakdown of Lignin, Vol. WO/2008/106811.

Voitl, T., Rudolf von Rohr, P. 2008. Oxidation of Lignin Using Aqueous Polyoxometalates in the Presence of Alcohols. *ChemSusChem*, 1(8-9), 763-769.

Wayman, M., Lora, J. H. 1978. Aspen autohydrolysis—The effects of 2-naphtol and other aromatic compounds. Tappi, 61(6), 55-57.

Werhan, H., Mir, J. M., Voitl, T., Rudolf von Rohr, P. 2011. Acidic oxidation of kraft lignin into aromatic monomers catalyzed by transition metal salts. *Holzforschung*, - - - .

Wollrab, A. 2009. *Organische Chemie—Eine Einführung für Lehramts-and Nebenfachstudenten.* 3 ed. Springer-Verlag, Berlin.

Yu, Z., Jameel, H., Chang, H.-m., Park, S. 2011. The effect of delignification of forest biomass on enzymatic hydrolysis. *Bioresource Technology*, 102(19), 9083-9089.

The invention claimed is:

1. A process for the treatment of lignocellulosic biomass for producing biofuels/chemicals and/or a lignin fraction for chemical production, comprising:

a) providing a lignocellulosic biomass;
b) treating the lignocellulosic biomass with water or steam having a temperature of from about 100° C. to about 260° C. and at least one carbonium ion scavenger, thereby producing a biomass comprising cellulose and pre-depolymerized lignin, wherein the treating with water or steam is a multi-step treatment comprising a mild treatment stage comprising treatment at a temperature above 100° C. and below 190° C. for greater than 60 minutes, and the harsh treatment stage comprising treatment at a temperature of from 190° C. to 260° C. for from 3 to 60 minutes; and
c) adding one or more cellulolytic enzymes to the biomass comprising cellulose and pre-depolymerized lignin, thereby hydrolyzing the cellulose and producing a mixture comprising sugars and pre-depolymerized lignin.

2. The process according to claim 1, wherein the carbonium ion scavenger is a solid, liquid or gaseous carbonium ion scavenger, or a mixture of scavengers, and wherein the carbonium ion scavenger is selected from the group consisting of: substituted and non-substituted monocyclic aromatic compounds, phenol and alkylphenols, guaiacol and alkylguaiacols, hydroxybenzoic acids, cresols, xylenols, xylenes, catechols and alkylcatechols, hydroquinone and alkylhydroquinones, anthraquinone and alkylantraquinones, anisole and alkylanisoles, tryptophan, polycyclic non-substituted aromatics, anthracene, pyrene, substituted polycyclic aromatics, 7-hydroxyquinoline, and naphthols and alkylated naphthols.

3. The process according to claim 2, wherein the carbonium ion scavenger is a sulfur-containing aromatic compound.

4. The process according to claim 2, wherein the carbonium ion scavenger is selected from the group consisting of methionine, silanes, amines, salts, silicone compounds, hydrazines, organic acids, and alcohols.

5. The process according to claim 1, wherein the carbonium ion scavenger is used to prevent the condensation of lignin fragments with sugar degradation products.

6. The process according to claim 1, further comprising:
(d) subjecting the pre-depolymerized lignin to one or more of oxidation, hydrogenation, hydrogenolysis, or pyrolysis, thereby producing lignin.

7. The process according to claim 6, wherein the resulting lignin is used as a raw material for the production of aromatic chemicals, which are recycled as single products or as a mixture of products to the treating stage to be used as the carbonium ion scavengers.

8. The process according to claim 6, wherein the lignin is used as a component in phenol-based polymers.

9. The process according to claim 1, wherein the treated biomass is used for producing a targeted lignin product formation by the use of tailor-made carbonium ion scavengers.

10. The process according to claim 1, wherein the treating step occurs under acidic conditions.

11. The process according to claim 1, wherein the organic feedstock contains lignocellulosic material containing fermentable carbohydrates selected from the group consisting of softwoods, hardwoods, herbs, and agricultural residues.

12. The process according to claim 1, wherein the treating step is carried out under inert gas, oxygen containing, ozone containing or hydrogen containing atmosphere.

13. The process according to claim 1, wherein the temperature of the hot water or steam is within the range from about 190 to 240° C. and wherein the pressure in the hot water treatment stage is maintained within the range from about 0 to 500 bar.

14. The process according to claim 1, wherein the pH in the treating step is adjusted by the addition of acids.

15. The process according to claim 1, wherein the pH in the treating step is adjusted by the addition of bases.

16. The process according to claim 1, wherein lignocellulosic material in the treating step is treated as suspension in a liquid phase, directly with steam or by steam explosion and wherein the water to dry biomass ratio is in the range between 1:1 and 100:1.

17. The process according to claim 1, wherein the quantity of the carbonium ion scavenger added in the treating step is in a range between 0.01 to 10% w/w based on dry biomass loading.

18. The process according to claim 1, wherein the carbonium ion scavenger is added by direct addition to a liquid phase before or during the treating step or impregnation of the biomass prior to the treating step.

19. The process according to claim 1, wherein unreacted carbonium ion scavenger is recovered after the treating step and recycled to the treating step.

20. The process according to claim 1, wherein the treated biomass is washed before entering the enzymatic hydrolysis stage.

21. The process according to claim 1, wherein the at least one carbonium ion scavenger is added during the harsh treatment stage.

22. A process for the treatment of lignocellulosic biomass for producing biofuels/chemicals and/or a lignin fraction for chemical production, comprising:
a) providing a lignocellulosic biomass;
b) treating the lignocellulosic biomass in an oxygen-free environment with water or steam having a temperature of from about 100° C. to about 260° C. and at least one carbonium ion scavenger, thereby producing a biomass comprising cellulose and pre-depolymerized lignin, wherein the treating with water or steam is a multi-step treatment comprising a mild treatment stage comprising treatment at a temperature above 100° C. and below 190° C. for greater than 60 minutes, and the harsh treatment stage comprising treatment at a temperature of from 190° C. to 260° C. for from 3 to 60 minutes; and
c) adding one or more cellulolytic enzymes to the biomass comprising cellulose and pre-depolymerized lignin, thereby hydrolyzing the cellulose and producing a mixture comprising sugars and pre-depolymerized lignin.

23. A process for the treatment of lignocellulosic biomass for producing biofuels/chemicals and/or a lignin fraction for chemical production, comprising:
a) adding a lignocellulosic biomass to a reactor;
b) removing oxygen from the reactor;
c) treating the lignocellulosic biomass with water or steam having a temperature above 100° C. and below 190° C. for greater than 60 minutes;
d) adding one or more cellulolytic enzymes to the biomass;
e) recovering sugar from the treated lignocellulosic biomass;
f) treating the lignocellulosic biomass with water or steam having a temperature of from 190° C. to 260° C. for from 3 to 60 minutes; and
g) adding one or more cellulolytic enzymes to the biomass, wherein a carbonium ion scavenger is added to the lignocellulosic biomass prior to or during the treating steps.

24. A process for the treatment of lignocellulosic biomass for producing biofuels/chemicals and/or a lignin fraction for chemical production, comprising:
  a) providing a lignocellulosic biomass;
  b) treating the lignocellulosic biomass with water or steam having a temperature above 100° C. and below 190° C. for greater than 60 minutes;
  c) adding a carbonium ion scavenger to the lignocellulosic biomass and treating the scavenger and lignocellulosic biomass with water or steam having a temperature of from 190° C. to 260° C. for from 3 to 60 minutes; and
  d) adding one or more cellulolytic enzymes to the biomass.

* * * * *